(12) United States Patent
Cohen et al.

(10) Patent No.: US 11,163,893 B2
(45) Date of Patent: Nov. 2, 2021

(54) METHODS AND SYSTEMS FOR A REDUNDANTLY SECURE DATA STORE USING INDEPENDENT NETWORKS

(71) Applicant: nsKnox Technologies LTD., Petach Tikva (IL)

(72) Inventors: Alon N. Cohen, Zichron Yaacov (IL); Ilan Shiber, Ganei Tikva (IL); Sagi Vizner, Netanya (IL); Yoav Hermon, Rishon LeTsion (IL)

(73) Assignee: nsKnox Technologies Ltd., Petah Tikvah (IL)

( * ) Notice: Subject to any disclaimer, the term of this patent is extended or adjusted under 35 U.S.C. 154(b) by 193 days.

(21) Appl. No.: 16/317,033

(22) PCT Filed: Jul. 13, 2016

(86) PCT No.: PCT/IL2016/050756
§ 371 (c)(1),
(2) Date: Jan. 11, 2019

(87) PCT Pub. No.: WO2018/011779
PCT Pub. Date: Jan. 18, 2018

(65) Prior Publication Data
US 2019/0251269 A1 Aug. 15, 2019

(51) Int. Cl.
*G06F 21/60* (2013.01)
*G06F 21/62* (2013.01)
(Continued)

(52) U.S. Cl.
CPC ............ *G06F 21/602* (2013.01); *G06F 16/00* (2019.01); *G06F 16/252* (2019.01); *G06F 21/62* (2013.01);
(Continued)

(58) Field of Classification Search
CPC .... G06F 21/602; G06F 21/6218; G06F 21/62; G06F 16/00; G06F 16/252;
(Continued)

(56) References Cited

U.S. PATENT DOCUMENTS

| | | | |
|---|---|---|---|
| 2012/0221856 A1* | 8/2012 | Orsini | H04L 63/0428 713/167 |
| 2013/0246812 A1* | 9/2013 | Resch | G06F 12/1408 713/193 |
| 2014/0372770 A1* | 12/2014 | O'Hare | G06F 16/22 713/189 |

* cited by examiner

*Primary Examiner* — Jeffrey C Pwu
*Assistant Examiner* — Mayasa A. Shaawat
(74) *Attorney, Agent, or Firm* — Reuven K. Mouallem; FlashPoint IP Ltd.

(57) ABSTRACT

The present invention discloses methods and systems for redundantly securing data using an array of independent networks. Methods include the steps of: upon receiving a storage request and secret data for securely storing the secret data, independently requesting random data from each of at least one independent partner network out of an array of at least two independent partner networks; independently receiving the random data from each of at least one independent partner network, wherein respective random data is also stored on a respective independent partner network; cumulatively calculating complementary data as an encrypted form of the secret data with a complement function using the random data; and sending the complementary data to an independent storage partner network for storage, wherein the independent storage partner network is part of the array, and wherein the independent storage partner network is independent from at least one independent partner network.

21 Claims, 2 Drawing Sheets

Exemplary Embodiment

(51) Int. Cl.
*G06Q 10/00* (2012.01)
*G06Q 50/26* (2012.01)
*G06Q 50/22* (2018.01)
*G06Q 40/00* (2012.01)
*G06F 16/00* (2019.01)
*G06F 16/25* (2019.01)
*H04L 9/08* (2006.01)
*H04L 9/32* (2006.01)

(52) U.S. Cl.
CPC ......... *G06F 21/6218* (2013.01); *G06Q 10/00* (2013.01); *G06Q 40/00* (2013.01); *G06Q 50/22* (2013.01); *G06Q 50/26* (2013.01); *H04L 9/0869* (2013.01); *H04L 9/32* (2013.01); *H04L 9/3228* (2013.01); *G06F 2221/2107* (2013.01)

(58) Field of Classification Search
CPC ............ G06F 2221/2107; G06Q 10/00; G06Q 50/26; G06Q 50/22; G06Q 40/00; H04L 9/0869; H04L 9/32; H04L 9/3228; G16H 10/60
See application file for complete search history.

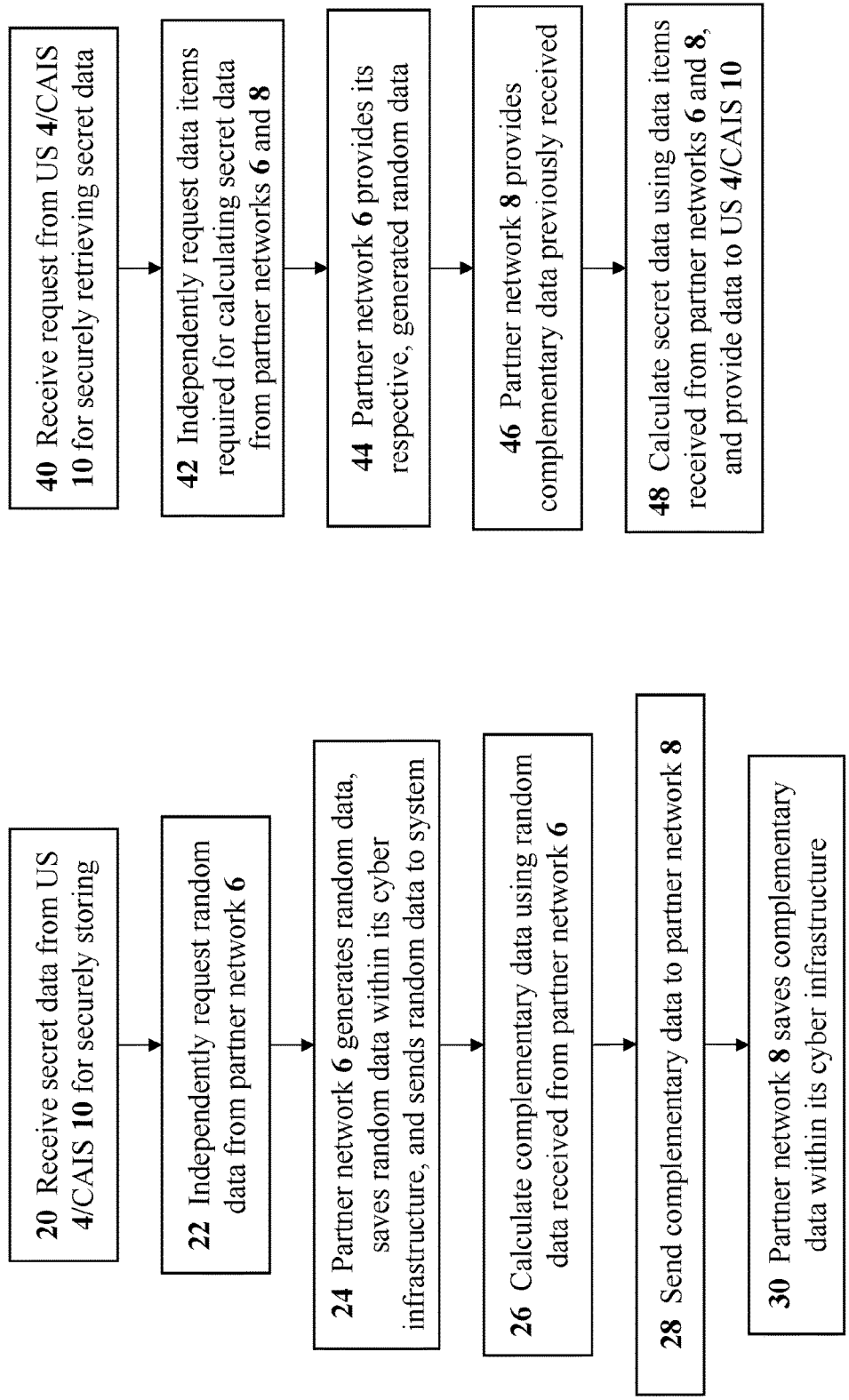

METHODS AND SYSTEMS FOR A REDUNDANTLY SECURE DATA STORE USING INDEPENDENT NETWORKS

FIELD AND BACKGROUND OF THE INVENTION

The present invention relates to methods and systems for a redundantly-secure data store using independent networks. A redundantly-secure data store is based on a distributed and cooperative process for cryptographically splitting information over an array of independent networks, and provides enterprises and consumers with a redundant cyber protection for data and transactions over the cyberspace. Redundant cyber protection is resistant to cybersecurity flaws in any single network.

In modern times, computer systems play the dominant role in which sensitive information is managed and stored. Such information might be Personally-Identifiable Information (PII) (e.g., social security number and address), Personal Health Information (PHI) (e.g., private medical records), and/or sensitive financial information (e.g., credit card numbers).

Exposure of sensitive information may have serious impact on individuals, businesses, institutions, and governments. Thus, data owners (e.g., financial institutions, hospitals, and service providers) spend large sums of money in developing and deploying cybersecurity systems that protect such sensitive information.

Unfortunately, no organization seems to be impervious to advanced cyber-attacks. Recent examples include breaches to banks (e.g., JP Morgan chase), insurance companies (e.g., Anthem), and even governments (e.g., United States Office of Personnel Management).

Such attacks have become somewhat common due in part to the fact that the strength of a network is determined by the strength of its weakest link. In the case of an enterprise network, the chain is very long and contains many links. Enterprise networks are composed, by nature, of many dynamic digital components as well as human personnel. So, every part of the network (digital or human) might become a potential penetration point. Therefore, such complex networks are more vulnerable, causing security flaws to inevitably arise. Given enough time and effort, malicious parties will find the way to exploit them.

In the prior art, tokenization is a well-known process of using a different entity (the "tokenization service") for storing sensitive data. During the tokenization process, the sensitive data is sent to the tokenization service, which stores the data in a database. The tokenization service returns, in response, a token which represents the sensitive data. The data owner substitutes the sensitive data with the token. When the data owner needs the actual sensitive data, the owner sends the token to the tokenization service and retrieves the original data.

Such tokenization methods provide no redundancy. That is, the sensitive data is stored and protected by a single network and a single security infrastructure (i.e., those of the token provider). In such configurations, breaching a single network would be enough to maliciously access the sensitive data. Moreover, such tokenization methods inherently require the tokenization service to have full knowledge of the sensitive data in the sense that the tokenization service receives the actual data, becoming aware of its secret nature.

Data encryption is a well-known process involving encrypting data before saving, thereby protecting the data while stored since a decryption key is required in order to access the data. Such methods use a common secret (i.e., the encryption key). The sensitive data (while encrypted) and the decryption key are both stored and managed by the same network, the owner's network in such a case. Breaching such a network might expose both the encrypted data and the decryption key, and as a result the actual data. Moreover, the encryption/decryption key itself is a single point of failure, since once the key is exposed all encrypted data is at risk.

Cryptographically splitting data, typically implemented with a xor operation, or using Shamir's scheme is a known mechanism for cryptographically turning a piece of information into a set of two or more data parts. Each part can be stored on a separate media device or server. Since all data parts (or most of them in some implementations) are necessary for obtaining the original information, an increased level of security may be achieved. Such a security mechanism by itself also fails to provide redundant cyber protection since the "data-split" process is handled locally within a single network. As such, the data-split process is vulnerable to successful cyber-attacks just as encryption schemes implemented in such a single network.

It would be desirable to have methods and systems for a redundantly-secure data store for achieving redundant cyber protection utilizing a distributed and cooperative process for cryptographically splitting information over an array of independent networks. Such methods and systems would, inter alia, overcome the various limitations mentioned above, and would provide a redundantly-secure solution for the storage, exchange, and/or sharing of sensitive information over cyberspace.

SUMMARY

It is the purpose of the present invention to provide methods and systems for a redundantly-secure data store based on a distributed and cooperative process for cryptographically splitting information over an array of independent networks.

While no single organization seems impervious on its own to advanced cyber-attacks, a distributed and cooperative process that allows multiple independent networks to "join forces" is able to significantly reduce the risk of a massive data breach for information handled and stored by such an array of networks.

To overcome the inherent risk of a cybersecurity failure in any single network and its cybersecurity infrastructure, embodiments of the present invention offer a resistance to cybersecurity flaws in any single network through cryptographically splitting information over an array of two or more independent networks. Such a resistance enables highly-secure storage, exchange, and/or sharing of information over the cyberspace, without being dependent on the security strength of any single network and without a need to trust any single network.

A distributed and cooperative process for cryptographically splitting information over an array of independent networks must adhere to all of the following criteria.

1. The data-split process (i.e., random number generation and complementary number calculation explained in detail below) is distributed and co-handled over multiple, independent networks.
2. The storage of such data parts generated above in Point 1 is also distributed in the sense that each and every data part is stored within an independent network.

3. Access control (i.e., authentication and authorization) is also distributed in a way that access control over each and every data part is independently governed by a separate network.

By cryptographically splitting data items of a person or an enterprise over an array of independent networks, each network in such an array has no knowledge (i.e., zero knowledge) of the actual data that such an array cumulatively holds. As a result, a potential attacker would have to break into each and every network in such an array, almost simultaneously, in order to gain access to, or to fraudulently change, any data element stored in such an array. Since such networks are independent, each having its own independent cybersecurity infrastructure, such a simultaneous breach becomes significantly less likely.

Forming such an array of independent networks could include networks of business partners, service providers, or networks belonging to the entity that uses such a system, as long as all such networks are independent of each other in the sense of their cybersecurity infrastructure and their security personnel.

It is noted that the term "exemplary" is used herein to refer to examples of embodiments and/or implementations, and is not meant to necessarily convey a more-desirable use-case. Similarly, the terms "alternative" and "alternatively" are used herein to refer to an example out of an assortment of contemplated embodiments and/or implementations, and is not meant to necessarily convey a more-desirable use-case. Therefore, it is understood from the above that "exemplary" and "alternative" may be applied herein to multiple embodiments and/or implementations. Various combinations of such alternative and/or exemplary embodiments are also contemplated herein.

For purposes of clarity, several terms are defined herein. The term "owner" is used herein to refer to any user or client system who owns data. The term "partner networks" is used herein to refer to multiple, independent networks in which the term "independent" is used in order to emphasize that each partner is a separate entity with its own secure infrastructure, and does not depend or rely in any way on any other partner network.

The terms "redundant," "redundantly-secure," and "redundantly securing" are used herein to refer to the cumulative implementation of more than one security measure in order to enhance cybersecurity performance. This is akin to the standard computer-industry term "RAID" (redundant array of independent disks) for a data-storage virtualization technology that combines multiple physical disk drive components into a single logical unit for the purposes of data redundancy, performance improvement, or both.

Embodiments of the present invention enable an owner to protect data using a set of partner networks. In such configurations, due to the nature of the distributed and cooperative process for cryptographically splitting information over an array of independent network, which forces an attacker to breach all independent networks (in a limited amount of time) in order to gain access to a protected resource, data security doesn't depend on the strength of a single network or link. The cumulative security strength of all such networks forming the array is the de facto strength of the array.

Embodiments of the present invention provide various security features and benefits beyond state-of-the-art security techniques. Such features and benefits include the following aspects.

Redundant Protection for Data "At Rest" (i.e., stored data)—the data is not encrypted using a shared and common secret, but rather "encrypted" (or "cryptosplit") using N different random parameters (i.e., data parts) obtained (and stored for future retrieval) from N independent partner networks. Hence, if an attacker manages to obtain the data parts stored in N−1 partner networks, it is still useless for revealing and accessing the data. Practically, an attacker has to penetrate N partner network in order to get all data parts which are necessary in order to "decrypt" the data (such an attacker may also have to somehow get hold of the pointers which link the various data parts to each other—the "data-part mapping," which is typically stored inside the owner's network itself). The fact that each network is completely independent (i.e., uses different personnel, different security methods, and possibly different technologies) ensures that a security flaw in one network will not assist in any way in penetrating other networks.

Zero Knowledge Store—for any given partner network, the data part stored in the network is just a meaningless random value. Partner networks are unaware of the original data cumulatively stored within them. Hence, every partner network is completely "blind" to the actual data that the network takes part in storing (i.e., the network has "zero knowledge" of its value). Such benefit is important for the actual owners of the information to ensure that sensitive data is not exposed to any of the partner networks, and no such network can, even if it tries to, obtain/decrypt/expose the original value.

Mitigating the Scope of Data Exposure—the ability of data owners to "export" the storage of their most sensitive information to a group of business partners and trusted service providers enables the owners to mitigate the scope of a data exposure, to reduce their cybersecurity costs, and to easily comply with essential security standards and regulations (e.g., PCI DSS—the Payment Card Industry Data Security Standard).

External & Independent Audit Log—hackers, in general, exploit the ability to "cover their tracks" in data-breach attacks. That typically means altering audit and security logs to conceal any sign of data being wrongly exposed. By forcing attackers to access multiple, remote and independent networks, each having its own independent audit log, in order to retrieve data, it becomes significantly more difficult for such attackers to hide their activities.

External & Independent Access Control—data owners can define various authentication and authorization policies on each network in such an array—policies that might restrict access according to, but not limited to, time, location, and number of accesses, all effectively enforced by an independent partner network, making a successful attack much harder to accomplish.

Therefore, according to the present invention, there is provided for the first time a method for redundantly securing data using an array of independent networks, the method including the steps of: (a) upon receiving a storage request and secret data for securely storing the secret data, independently requesting random data from each of at least one independent partner network out of an array of at least two independent partner networks; (b) independently receiving the random data from each of at least one independent partner network, wherein respective random data is also stored on a respective independent partner network; (c) cumulatively calculating complementary data as an encrypted form of the secret data with a complement function using the random data; and (d) sending the complementary data to an independent storage partner network for storage, wherein the independent storage partner network is part of the array, and wherein the independent storage partner network is independent from at least one independent partner network.

Alternatively, the random data are one-time data items.

Alternatively, the encrypted form cannot be decrypted to produce the secret data without using the random data and the complementary data.

Alternatively, the complement function is a XOR operation.

Alternatively, the storage request requires independent authentication to be considered a valid request, and wherein at least one independent partner network and the independent storage partner network each require independent authentication to be considered partner networks.

Most alternatively, the independent authentication employs at least one technique selected from the group consisting of: a user/password authentication, a private/public key authentication, and a biometric identification.

Alternatively, the method further includes the steps of: (e) upon receiving a retrieval request for securely retrieving the secret data, independently requesting the random data from each of at least one independent partner network; (f) independently requesting the complementary data from the independent storage partner network; (g) respectively receiving independently the random data and the complementary data from each of at least one independent partner network and the independent storage partner network; and (h) cumulatively calculating the secret data as a decrypted form of the complementary data with a corresponding complement function using the random data.

Most alternatively, the decrypted form can only be produced using the random data and the complementary data.

According to the present invention, there is provided for the first time a system for redundantly securing data using an array of independent networks, the system including: (a) a CPU for performing computational operations; (b) a memory module for storing data; (c) a network connection for communicating across a data-exchange protocol system; and (d) a secure-storage module configured for: (i) upon receiving a storage request and secret data for securely storing the secret data, independently requesting random data from each of at least one independent partner network out of an array of at least two independent partner networks; (ii) independently receiving the random data from each of at least one independent partner network, wherein respective random data is also stored on a respective independent partner network; (iii) cumulatively calculating complementary data as an encrypted form of the secret data with a complement function using the random data; and (iv) sending the complementary data to an independent storage partner network for storage, wherein the independent storage partner network is part of the array, and wherein the independent storage partner network is independent from at least one independent partner network.

Alternatively, the random data are one-time data items.

Alternatively, the encrypted form cannot be decrypted to produce the secret data without using the random data and the complementary data.

Alternatively, the complement function is a XOR operation.

Alternatively, the storage request requires independent authentication to be considered a valid request, and wherein at least one independent partner network and the independent storage partner network each require independent authentication to be considered partner networks.

Most alternatively, the independent authentication employs at least one technique selected from the group consisting of: a user/password authentication, a private/public key authentication, and a biometric identification.

Alternatively, the system further includes: (e) a secure-retrieval module configured for: (i) upon receiving a retrieval request for securely retrieving the secret data, independently requesting the random data from each of at least one independent partner network; (ii) independently requesting the complementary data from the independent storage partner network; (iii) respectively receiving independently the random data and the complementary data from each of at least one independent partner network and the independent storage partner network; and (iv) cumulatively calculating the secret data as a decrypted form of the complementary data with a corresponding complement function using the random data.

Most alternatively, the decrypted form can only be produced using the random data and the complementary data.

According to the present invention, there is provided for the first time a non-transitory computer-readable storage medium, having computer-readable code embodied on the non-transitory computer-readable storage medium, for redundantly securing data using an array of independent networks, the computer-readable code including: (a) program code for, upon receiving a storage request and secret data for securely storing the secret data, independently requesting random data from each of at least one independent partner network out of an array of at least two independent partner networks; (b) program code for independently receiving the random data from each of at least one independent partner network, wherein respective random data is also stored on a respective independent partner network; (c) program code for cumulatively calculating complementary data as an encrypted form of the secret data with a complement function using the random data; and (d) program code for sending the complementary data to an independent storage partner network for storage, wherein the independent storage partner network is part of the array, and wherein the independent storage partner network is independent from at least one independent partner network.

Alternatively, the random data are one-time data items.

Alternatively, the encrypted form cannot be decrypted to produce the secret data without using the random data and the complementary data.

Alternatively, the complement function is a XOR operation.

Alternatively, the storage request requires independent authentication to be considered a valid request, and wherein at least one independent partner network and the independent storage partner network each require independent authentication to be considered partner networks.

Most alternatively, the independent authentication employs at least one technique selected from the group consisting of: a user/password authentication, a private/public key authentication, and a biometric identification.

Alternatively, the computer-readable code further includes: (e) program code for, upon receiving a retrieval request for securely retrieving the secret data, independently requesting the random data from each of at least one independent partner network; (f) program code for independently requesting the complementary data from the independent storage partner network; (g) program code for respectively receiving independently the random data and the complementary data from each of at least one independent partner network and the independent storage partner network; and (h) program code for cumulatively calculating the secret data as a decrypted form of the complementary data with a corresponding complement function using the random data.

Most alternatively, the decrypted form can only be produced using the random data and the complementary data.

These and further embodiments will be apparent from the detailed description and examples that follow.

BRIEF DESCRIPTION OF THE DRAWINGS

The present invention is herein described, by way of example only, with reference to the accompanying drawings, wherein:

FIG. 2 is a simplified flowchart of the major process steps for securely storing sensitive data on a redundantly-secure data store using independent networks, according to embodiments of the present invention.

FIG. 3 is a simplified flowchart of the major process steps for retrieving sensitive data from a redundantly-secure data store using independent networks, according to embodiments of the present invention.

DESCRIPTION OF THE ILLUSTRATIVE EMBODIMENTS

Figure 1:
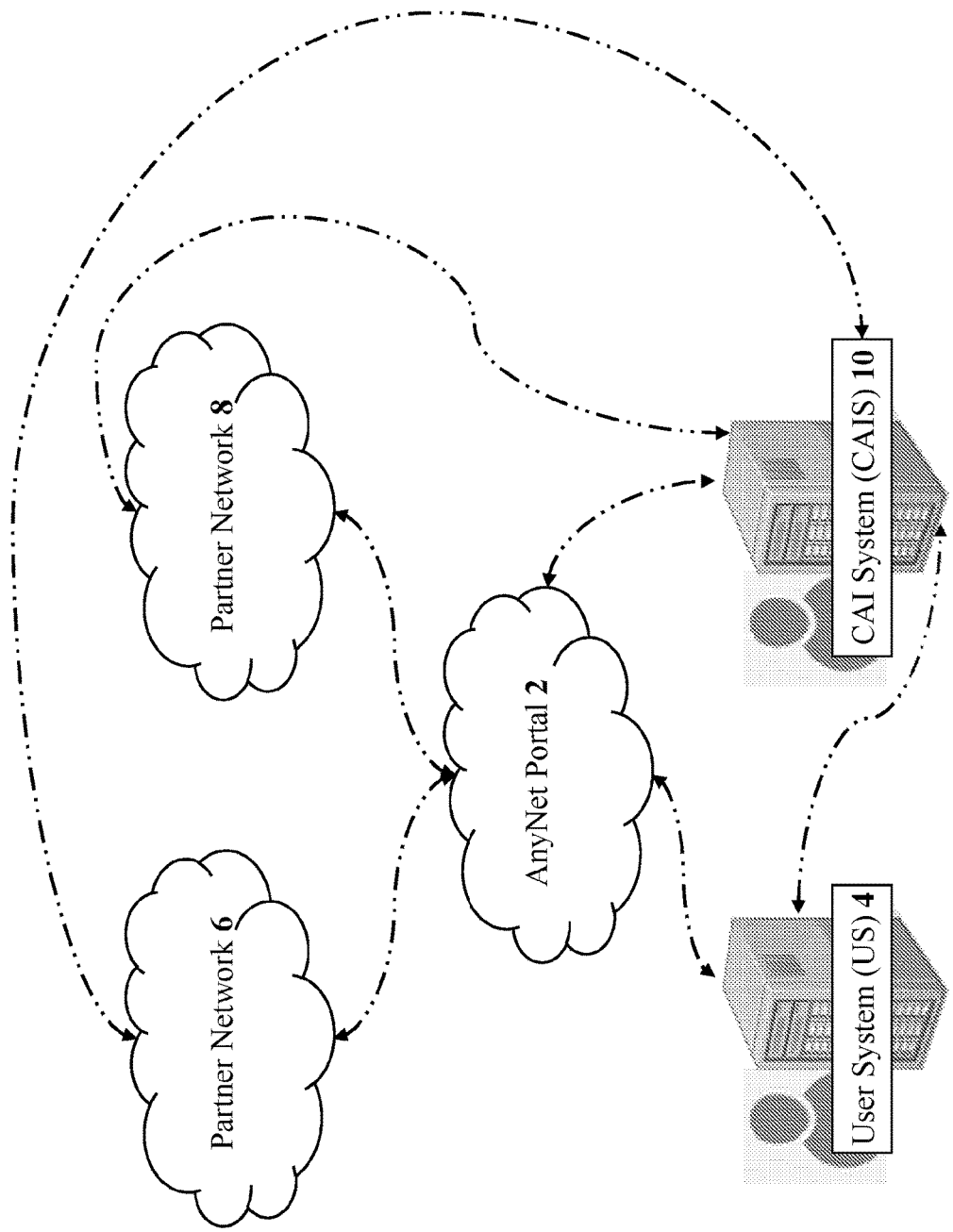
FIG. 1 is a simplified high-level schematic diagram of a typical system architecture for a redundantly-secure data store using independent networks, according to embodiments of the present invention.

The present invention relates to methods and systems for a redundantly-secure data store based on a distributed and cooperative process for cryptographically splitting information over an array of independent networks. The principles and operation for providing such methods and systems, according to the present invention, may be better understood with reference to the accompanying description and the drawings.

Referring to the drawings, FIG. 1 is a simplified high-level schematic diagram of a typical system architecture for a redundantly-secure data store using independent networks, according to embodiments of the present invention. An "AnyNet" portal 2 is used to represent the partner-network implementation system, which manages the storage and retrieval of secret data for a User System (US) 4 (i.e., a data owner operationally connected to AnyNet portal 2 or any other computer system exchanging data with a US of AnyNet portal 2). AnyNet portal 2 is further operationally connected independently to partner networks 6 and 8. A Configured, Authorized, Initiating System is also shown having similar attributes to US 4 with the addition of being configured for secure data exchange by AnyNet portal 2 as described below, hereinafter referred to as a CAI System (CAIS) 10. In the exemplary embodiment of FIG. 1, two partner networks are shown; however, the number of partner networks implemented may be increased based on security requirements and limitations.

FIG. 2 is a simplified flowchart of the major process steps for securely storing sensitive data on a redundantly-secure data store using independent networks, according to embodiments of the present invention. The process starts when US 4 or CAIS 10 sends secret data to AnyNet portal 2 for securely storing (Step 20). Such data may be sent directly by CAIS 10 to its recipient since CAIS 10 can provide proper authorization once configuration settings from AnyNet portal 2 have been activated in CAIS 10.

AnyNet portal 2 or CAIS 10 independently requests random data from partner network 6 (and all other partner networks except the one storing the complementary data described below (i.e., partner network 8) in a multi-network implementation) (Step 22). Partner network 6 generates the random data, saves the random data within its cyber infrastructure, and sends the random data to AnyNet portal 2 or to CAIS 10 (Step 24).

AnyNet portal 2 or CAIS 10 calculates complementary data using the random data received from partner network 6 (Step 26). AnyNet portal 2 or CAIS 10 then sends the complementary data to partner network 8 (Step 28). Partner network 8 saves the complementary data within its cyber infrastructure (Step 30). Thus, cryptographically-split data is stored among partner networks 6 and 8 until the data is retrieved by AnyNet portal 2 or CAIS 10.

FIG. 3 is a simplified flowchart of the major process steps for retrieving sensitive data from a redundantly-secure data store using independent networks, according to embodiments of the present invention. The process starts when US 4 or CAIS 10 requests secret data that was securely stored by AnyNet portal 2 or CAIS 10 among the partner networks (Step 40).

AnyNet portal 2 or CAIS 10 independently requests partner networks 6 and 8 for the data items required for calculating the secret data (Step 42). Partner network 6 validates the credentials of the request, and given proper credentials, provides its respective random data generated in Step 24 of FIG. 2 (Step 44 of FIG. 3), while partner network 8 also validates the credentials of the request, and given proper credentials, provides the complementary data saved in Step 30 of FIG. 2 (Step 46 of FIG. 3). In implementations, AnyNet portal 2 or CAIS 10 may request the specific data items using a data-item identifier that was provided by partner networks 6 and 8 during the process of storing the secret data. AnyNet portal 2 or CAIS 10 calculates the secret data using the data items received from partner networks 6 and 8, and provides the data to US 4 or to CAIS 10 (Step 48).

To illustrate a typical use-case and provide implementation details of the exemplary embodiments outlined in FIGS. 1-3, consider the scenario in which an owner network (as represented by AnyNet portal 2, hereinafter referred to as AnyNet) wants to save a Social Security Number (SSN) for a client (as represented by US 4 or CAIS 10 above). Since the privacy of AnyNet's clients is important, the SSN should be kept in a secure manner. By using the cumulative protection of multiple, independent networks (as represented by partner networks 6 and 8 above), such secure storage can be achieved by cumulatively utilizing the security infrastructure of the networks in the following manner.

1. AnyNet wants to securely store data item d. AnyNet uses a series of N independent partner networks, $(p_1, p_2, \ldots, p_n)$.
2. AnyNet requests N−1 partner networks, $(p_1, p_2, p_{n-1})$, to each generate one-time random data items.
3. Each of the N−1 partner networks generates (using any known random number generator (RNG) technique) a random data item, stores the random data item securely within its cyber infrastructure, and sends the random data item to AnyNet.
4. AnyNet uses the series of N−1 random data items, $(r_1, r_2, \ldots, r_{n-1})$, and calculates c with a complement function, comp, in which $c=comp(r_1, r_2, \ldots, r_{n-1}, d)$. The calculated result c is then sent, and stored in the remaining partner network, $p_n$. Note that a mandatory property of comp is that in order to retrieve d, one must know c as well as all the other random data items ($r_1$, $r_2$, ..., $r_{n-1}$).

5. When the storing process is complete, it is noted that AnyNet does not save d, any of the random data items, nor the complementary data item, c. The secret data item is practically stored amongst the partner networks ($p_1$ store $r_1$, $p_2$ stores $r_2$, $p_{n-1}$ stores $r_{n-1}$, and $p_n$ stores c).

6. When access to d is requested, one has to retrieve $r_1$, $r_2$, ..., $r_{n-1}$, c from the appropriate ($p_1$, $p_2$, ..., $p_n$) networks, and then calculate d using a corresponding complement function, $comp^{-1}$, in which $d=comp^{-1}(r_1, r_2, ..., r_{n-1}, c)$.

Every partner network independently protects its data item, ($r_1, r_2, ..., r_{n-1}, c$), and provides access to legitimate parties only (AnyNet, or any party authorized by AnyNet, in this case), using any conventional authentication/authorization methods, such as but not limited to user/password authentication, private/public key authentication, and biometric identification. Every functions that fulfills the following conditions may be used as comp and $comp^{-1}$.

(a) Given random data items ($r_1, r_2, ..., r_{n-1}$) and secret data d, comp can calculate c.
(b) Given the same random data items ($r_1, r_2, ..., r_{n-1}$) and the calculated c, $comp^{-1}$ can calculate d.
(c) $comp^{-1}$ can calculate d if and only if it knows ($r_1, r_2, ..., r_{n-1}$) and c.

A possible implementation for both the comp and $comp^{-1}$ functions is the xor operation. By performing a xor operation on the secret data, every bit of the data yields a complementary bit, and thus the resulting c (the complement data item of d). Thus, in order to calculate d, a xor operation is performed on the random data items and the complement data item c, producing the result d.

The examples used herein relate to N partner networks that would all have to be breached/legally accessed in order to gain access to the data. However, it is noted that in some implementations, for the sake of high availability and performance, it is possible to use a larger number of partner networks (e.g., M partner networks, wherein M>N) in which the data parts are stored, and from which any subset of N partner networks could be selected for retrieving and reconstructing the original data. Such installation may use Shamir's secret-sharing scheme or similar schemes rather than xor operation as the basis for the cryptographic splitting.

While the present invention has been described with respect to a limited number of embodiments, it will be appreciated that many variations, modifications, and other applications of the present invention may be made.

What is claimed is:

1. A method for redundantly securing data using an array of independent networks, the method comprising the steps of:

(a) upon receiving a storage request and secret data for securely storing said secret data, cryptographically splitting said secret data by independently requesting random data from each of at least one independent partner network out of an array of at least two independent partner networks, wherein said random data are one-time data items, and wherein the complete independence of each independent partner network of said array ensures that a security flaw in a given independent partner network will not assist in any way in penetrating other independent partner networks in said array;

(b) independently receiving said random data from each of said at least one independent partner network, wherein respective random data is stored on a respective independent partner network;

(c) cumulatively calculating complementary data as an encrypted form of said secret data with a complement function using said random data; and (d) sending said complementary data to an independent storage partner network for storage, wherein said independent storage partner network is part of said array, and wherein said independent storage partner network is independent from said at least one independent partner network; and wherein authentication and authorization are distributed in a way that access control over each and every data part is independently governed by a separate independent partner network;

wherein said step of cryptographically splitting results in each independent partner network of said array having zero knowledge of the actual data that said array cumulatively holds; and wherein said zero knowledge is defined to mean that said data parts stored in any given independent partner network are meaningless random values to said given independent partner network, preventing said given independent partner network from obtaining, decrypting, or exposing said secret data.

2. The method of claim 1, wherein said encrypted form cannot be decrypted to produce said secret data without using said random data and said complementary data.

3. The method of claim 1, wherein accessing said secret data requires access to said each and every data part on all said independent partner networks storing said data parts and access to respective data-part mapping pointers.

4. The method of claim 1, wherein said storage request requires independent authentication to be considered a valid request, and wherein said at least one independent partner network and said independent storage partner network each require independent authentication to be considered partner networks.

5. The method of claim 4, wherein said independent authentication employs at least one technique selected from the group consisting of: a user/password authentication, a private/public key authentication, and a biometric identification.

6. The method of claim 1, the method further comprising the steps of:

(e) upon receiving a retrieval request for securely retrieving said secret data, independently requesting said random data from each of said at least one independent partner network;

(f) independently requesting said complementary data from said independent storage partner network;

(g) respectively receiving independently said random data and said complementary data from each of said at least one independent partner network and said independent storage partner network; and (h) cumulatively calculating said secret data as a decrypted form of said complementary data with a corresponding complement function using said random data.

7. The method of claim 6, wherein said retrieval request requires independent authentication to be considered a valid request.

8. A system for redundantly securing data using an array of independent networks, the system comprising:

(a) a CPU for performing computational operations;
(b) a network connection for communicating across a data-exchange protocol system; and
(c) a memory for storing data and having computer-readable code embodied therein, wherein said computer-readable code includes:
  (i) program code for, upon receiving a storage request and secret data for securely storing said secret data, cryptographically splitting said secret data by independently requesting random data from each of at least one independent partner network out of an array of at least two independent partner networks, wherein said random data are one-time data items, and wherein the complete independence of each independent partner network of said array ensures that a security flaw in a given independent partner network will not assist in any way in penetrating other independent partner networks in said array;
  (ii) program code for independently receiving said random data from each of said at least one independent partner network, wherein respective random data is stored on a respective independent partner network;
  (iii) program code for cumulatively calculating complementary data as an encrypted form of said secret data with a complement function using said random data; and
  (iv) program code for sending said complementary data to an independent storage partner network for storage, wherein said independent storage partner network is part of said array, and wherein said independent storage partner network is independent from said at least one independent partner network; and
wherein authentication and authorization are distributed in a way that access control over each and every data part is independently governed by a separate independent partner network;
wherein said cryptographically splitting results in each independent partner network of said array having zero knowledge of the actual data that said array cumulatively holds; and
wherein said zero knowledge is defined to mean that said data parts stored in any given independent partner network are meaningless random values to said given independent partner network, preventing said given independent partner network from obtaining, decrypting, or exposing said secret data.

9. The system of claim 8, wherein said encrypted form cannot be decrypted to produce said secret data without using said random data and said complementary data.

10. The system of claim 8, wherein said accessing said secret data requires access to said each and every data part on all said independent partner networks storing said data parts and access to respective data-part mapping pointers.

11. The system of claim 8, wherein said storage request requires independent authentication to be considered a valid request, and wherein said at least one independent partner network and said independent storage partner network each require independent authentication to be considered partner networks.

12. The system of claim 11, wherein said independent authentication employs at least one technique selected from the group consisting of: a user/password authentication, a private/public key authentication, and a biometric identification.

13. The system of claim 8, wherein computer-readable code further includes:
  (v) program code for, upon receiving a retrieval request for securely retrieving said secret data, independently requesting said random data from each of said at least one independent partner network;
  (vi) program code for independently requesting said complementary data from said independent storage partner network;
  (vii) program code for respectively receiving independently said random data and said complementary data from each of said at least one independent partner network and said independent storage partner network; and
  (viii) program code for cumulatively calculating said secret data as a decrypted form of said complementary data with a corresponding complement function using said random data.

14. The system of claim 13, wherein said retrieval request requires independent authentication to be considered a valid request.

15. A non-transitory computer-readable storage medium, having computer-readable code embodied on the non-transitory computer-readable storage medium, for redundantly securing data using an array of independent networks, the computer-readable code comprising:
(a) program code for, upon receiving a storage request and secret data for securely storing said secret data, cryptographically splitting said secret data by independently requesting random data from each of at least one independent partner network out of an array of at least two independent partner networks, wherein said random data are one-time data items, and wherein the complete independence of each independent partner network of said array ensures that a security flaw in a given independent partner network will not assist in any way in penetrating other independent partner networks in said array;
(b) program code for independently receiving said random data from each of said at least one independent partner network, wherein respective random data is stored on a respective independent partner network;
(c) program code for cumulatively calculating complementary data as an encrypted form of said secret data with a complement function using said random data; and
(d) program code for sending said complementary data to an independent storage partner network for storage, wherein said independent storage partner network is part of said array, and wherein said independent storage partner network is independent from said at least one independent partner network; and
wherein authentication and authorization are distributed in a way that access control over each and every data part is independently governed by a separate independent partner network;
wherein said cryptographically splitting results in each independent partner network of said array having zero knowledge of the actual data that said array cumulatively holds; and
wherein said zero knowledge is defined to mean that said data parts stored in any given independent partner network are meaningless random values to said given independent partner network, preventing said given independent partner network from obtaining, decrypting, or exposing said secret data.

16. The non-transitory computer-readable storage medium of claim 15, wherein said encrypted form cannot be decrypted to produce said secret data without using said random data and said complementary data.

17. The non-transitory computer-readable storage medium of claim 15, wherein accessing said secret data requires access to said each and every data part on all said independent partner networks storing said data parts and access to respective data-part mapping pointers.

18. The non-transitory computer-readable storage medium of claim 15, wherein said storage request requires independent authentication to be considered a valid request, and wherein said at least one independent partner network and said independent storage partner network each require independent authentication to be considered partner networks.

19. The non-transitory computer-readable storage medium of claim 18, wherein said independent authentication employs at least one technique selected from the group consisting of: a user/password authentication, a private/public key authentication, and a biometric identification.

20. The non-transitory computer-readable storage medium of claim 15, the computer-readable code further comprising:

(e) program code for, upon receiving a retrieval request for securely retrieving said secret data, independently requesting said random data from each of said at least one independent partner network;

(f) program code for independently requesting said complementary data from said independent storage partner network;

(g) program code for respectively receiving independently said random data and said complementary data from each of said at least one independent partner network and said independent storage partner network; and (h) program code for cumulatively calculating said secret data as a decrypted form of said complementary data with a corresponding complement function using said random data.

21. The non-transitory computer-readable storage medium of claim 20, wherein said retrieval request requires independent authentication to be considered a valid request.

* * * * *